US008569005B2

(12) United States Patent
Thompson et al.

(10) Patent No.: US 8,569,005 B2
(45) Date of Patent: *Oct. 29, 2013

(54) CHLOROACETAMIDINE BASED INHIBITORS AND ACTIVITY BASED PROBES FOR THE PROTEIN ARGININE METHYTRANSFERASES

(71) Applicant: University of South Carolina, Columbia, SC (US)

(72) Inventors: Paul R. Thompson, Columbia, SC (US); Tanesha C. Osborne, Augusta, GA (US); Obiamaka Obianyo, Columbia, SC (US); Corey P. Causey, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/670,953

(22) Filed: Nov. 7, 2012

(65) Prior Publication Data

US 2013/0089882 A1     Apr. 11, 2013

Related U.S. Application Data

(62) Division of application No. 12/637,223, filed on Dec. 14, 2009, now Pat. No. 8,323,918.

(60) Provisional application No. 61/201,604, filed on Dec. 12, 2008.

(51) Int. Cl.
| | | |
|---|---|---|
| *C12Q 1/48* | (2006.01) | |
| *C12N 9/99* | (2006.01) | |
| *A61K 38/00* | (2006.01) | |
| *A61K 38/04* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |

(52) U.S. Cl.
USPC .............................. 435/15; 435/184; 530/326

(58) Field of Classification Search
None
See application file for complete search history.

(56) References Cited

U.S. PATENT DOCUMENTS 7,964,636 B2 *   6/2011   Thompson et al. ............ 514/454
8,323,918 B2 *  12/2012   Thompson et al. ............. 435/15

FOREIGN PATENT DOCUMENTS

WO    WO2007/056389    *   5/2007   .......... A61K 31/4192

OTHER PUBLICATIONS

Abramovich et al., "A Protein-Arginine Methyltransferase Binds to the Intracytoplasmic Domain of the IFNAR1 Chain in the Type I Interferon Receptor", The EMBO Journal, vol. 16, No. 2, 1997, pp. 260-266.
Bedford, "Arginine Methylation at a Glance", Journal of Cell Science, vol. 120, No. Pt. 24, Dec. 2007, pp. 4243-4246.
Chen et al., "Regulation of Transcription by a Protein Methyltransferase", Science, vol. 284, No. 5423, Jun. 1999, pp. 2174-2177.
Cook et al., "FBXO11/PRMT9, A New Protein arginine Methyltransferase, Symmetrically Dimethylates Arginine Residues", Biochemical and Biophysical Research Communications, vol. 342, No. 2, Apr. 2006, pp. 472-481.
El Messaoudi et al., "Coactivator-Associated Arginine Methyltransferase 1 (CARM1) is a Positive Regulator of the Cyclin E1 Gene". Proceedings for the National Academy of Sciences of the United States of America, vol. 103, No. 36, Sep. 2006, pp. 13351-13356.
Fielenbach et al., "DRE-1: An Evolutionarily Conserved F Box Protein that Regulates *C. elegans* Developmental Age", Developmental Cell, vol. 12, No. 3, Mar. 2007, pp. 443-455.
Gros et al., "Identification of New Drug Sensitivity Genes Using Genetic Suppressor Elements: Protein Arginine N-Methyltransferase Mediates Cell Sensitivity to DNA-Damaging Agents", Cancer Research, vol. 63, No. 1, Jan. 2003, pp. 164-171.
Hassa et al., "Protein Arginine Methyltransferase 1 Coactivates NF-kappaB-Dependent Gene Expression Synergistically with CARM1 and PARP1", Journal of Molecular Biology, vol. 377, No. 3, Mar. 2008, pp. 668-678.
Hong et al., "Aberrant Expression of CARM1, A Transcriptional Coactivator of Androgen Receptor, in the Development of Prostate Carcinoma and Androgen-Independent Status", Cancer, vol. 101, No. 1, Jul. 2004, pp. 83-89.
Koh et al., "Synergistic Enhancement of Nuclear Receptor Function by p160 Coactivators and Two Coactivators with Protein Methyltransferase Activities", Journal of Biological Chemistry, vol. 276, No. 2, Jan. 2001, pp. 1089-1098.
Krause et al., "Protein Arginine Methyltransferases: Evolution and Assessment of their Pharmacological and Therapeutic Potential", Pharmacology & Therapeutics, vol. 113, No. 1, Jan. 2007, pp. 50-87.
Lee et al., "Surface-Scanning Mutational Analysis of Protein Arginine Methyltransferase 1: Roles of Specific Amino Acids in Mnethyltransferase Substrate Specificity, Oligomerization, and Coactivator Function", Molecular Endocrinology, vol. 21, No. 6, Jun. 2007, pp. 1381-1393.
Lee et al., "Synergy Among Nuclear Receptor Coactivators: Selective Requirement for Protein Methyltransferase and Acetyltransferase Activities", Molecular and Cellular Biology, vol. 22, No. 11, Jun. 2002, pp. 3621-3632.

(Continued)

*Primary Examiner* — Marcela M Cordero Garcia
(74) *Attorney, Agent, or Firm* — Dority & Manning, P.A.

(57) ABSTRACT

In accordance with certain embodiments of the present disclosure, a protein arginine methyltransferase inhibitor is provided. The inhibitor comprises an amino acid peptide joined to a chloroacetamidine warhead.

4 Claims, 8 Drawing Sheets

(56) References Cited

OTHER PUBLICATIONS

Leiper et al., "Disruption of Methylarginine Metabolism Impairs Vascular Homeostasis" Nature Medicine, vol. 13, No. 2, Feb. 2007, pp. 198-203.

Le Romancer et al., "Regulation of Estrogen Rapid Signaling Through Arginine Methylation by PRMT1", Molecular Cell, vol. 31, No. 2, Jul. 2008, pp. 212-221.

Lin et al., "The Mammalian Immediate-Early TIS21 Protein and the Leukemia-Associated BIG1 Protein Interact with a Protein-Arginine N-Methyltransferase", The Journal of Biological Chemistry, vol. 271, No, 25, Jun. 1996, pp. 15034-15044.

Majumder et al., "Involvement of Arginine Methyltransferase CARM1 in Androgen Receptor Function and Prostate Cancer Cell Viability", Prostate, vol. 66, No. 12, Sep. 2006, pp. 1292-1301.

Obianyo et al., "Kinetic Mechanism of Protein Arginine Methyltransferase 1", Biochemistry, vol. 47, No. 39, Sep. 2008, pp. 10420-10427.

Osborne et al., "Protein Arginine Methyltransferase 1: Positively Charged Residues in Substrate Peptides Distal to the Site of Methylation are Important for Substrate Binding and Catalysis", Biochemistry, vol. 46, No. 46, Nov. 2007, pp. 13370-13381.

Pal et al., "Human SWI/SNF-Associated PRMT5 Methylates Histone H3 Arginine 8 and Negatively Regulates Expression of ST7 and NM23 Tumor Suppressor Genes", Molecular and Cellular Biology, vol. 24, No. 21, Nov. 2004, pp. 9630-9645.

Torres-Padilla at al., "Histone Arginine Methylation Regulates Pluripotency in the Early Mouse Embryo", Nature, vol. 445, No. 7124, Jan. 2007, pp. 214-218.

Tran et al., "The DDAH/ADMA/NOS Pathway", Atherosclerosis Supplements, vol. 4, No. 4, Dec. 2003, pp. 33-40.

Vallance et al., "Accumulation of an Endogenous Inhibitor of Nitric Oxide Synthesis in Chronic Renal Failure", Lancet, vol. 339, No. 8793, Mar. 1992, pp. 572-575.

Vallance et al., "Cardiovascular Biology of the Asymmetric Dimethylarginine: Dimethylarginine Dimethylaminohydrolase Pathway", Arteriosclerosis, Thrombosis, and Vascular Biology, vol. 24, No. 6, Apr. 2004, pp. 1023-1030.

Weerapana et al. "Tandem Orthogonal Proteolysis-Activity-Based Protein Profiling (TOP-ABPP)—A General Method for Mapping Sites of Probe Modification in Proteomes", Nature Protocols, vol. 2, No. 6, May 2007, pp. 1414-1425.

Zhang et al., "Structure of the Predominant Protein Arginine Methyltransferase PRMT1 and Analysis of its Binding to Substrate Peptides", Structure, vol. 11, No. 5, May 2003, pp. 509-520.

* cited by examiner

SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Orn

<400> SEQUENCE: 1

Ser Gly Xaa Gly Lys Gly Gly Lys Gly Leu Gly Lys Gly Gly Ala Lys
1               5                   10                  15

Arg His Arg Lys Val
            20

CHLOROACETAMIDINE BASED INHIBITORS AND ACTIVITY BASED PROBES FOR THE PROTEIN ARGININE METHYTRANSFERASES

CROSS-REFERENCE TO RELATED APPLICATION

The present application is a divisional of U.S. application Ser. No. 12/643,364 having a filing date of Dec. 21, 2009, which is based on and claims priority to U.S. Provisional Application 61/201,604 having a filing date of Dec. 12, 2008, which is incorporated by reference herein. Applicants claim priority to and benefit of all such applications and incorporate all such applications herein by reference.

BACKGROUND

Protein arginine methyltransferases (PRMTs) are eukaryotic enzymes that transfer a methyl group from S-adenosylmethionine (SAM) to the guanidino nitrogen of an arginine residue to form monomethyl arginine (MMA) as shown in FIG. 1. All PRMTs generate MMA, however they are classified as either type 1 or type 2, depending on the type of dimethylated arginine that they form. Type 1 PRMTs produce asymmetric dimethyl arginine (ADMA) upon the second round of methylation, whereas type 2 isozymes generate symmetric dimethyl arginine (SDMA). To date, eleven putative and confirmed PRMTs have been described in humans. PRMTs 1, 3, 4, 6, and 8 exhibit type 1 activity, while PRMTs 5, and 7 have type 2 activity. PRMTs 2 and 10 have not yet been shown to possess either type 1 or type 2 activity, thus they remain unclassified. Interestingly, PRMTs 9 and 11 possess catalytic domains that lack significant homology to the catalytic core domains of the other PRMT family members; thus these isozymes may not represent bona fide PRMTs.

PRMT1 is the predominant PRMT in mammalian cells and is thus responsible for the majority of the arginine methyltransferase activity in vivo. This enzyme is well conserved, both structurally and functionally, among eukaryotes. The human orthologue is composed of 353 amino acids (40.5 kDa) that primarily make-up the catalytic core. The structure of PRMT1 has been determined by X-ray crystallography and contains a Rossmann-type fold in the N-terminal half of the protein; this fold is involved in SAM binding as illustrated in FIG. 2. The C-terminal portion of the enzyme contains a consensus region, unique to PRMTs, and forms a β-barrel type fold that is thought to aid substrate binding. There is also a 3-helix 'arm' domain that protrudes from the C-terminal region of the protein; this arm is able to interact with the SAM binding domain of a second PRMT monomer to form a head-to-tail homodimer. Studies have demonstrated that the enzyme is only catalytically active in its dimeric form. Deletion or mutation of the helical arm prevents dimerization and results in catalytically inactive monomeric enzymes. Although the crystal structure of the enzyme is available, there is not a high-resolution structure of an enzyme:substrate complex in which residues N- and C-terminal to the site of methylation can be discerned. For this reason, the particular residues involved in substrate binding have yet to be identified.

PRMT1 was originally identified through its interactions with TIS21 and BTG1 proteins and the interferon-alpha receptor. The enzyme has since been implicated in an array of biological processes, including RNA metabolism, protein trafficking, cellular differentiation, and nuclear receptor mediated gene transcription. Current studies have primarily focused on the coactivator activity of the enzyme. In particular, PRMT1 has been found to interact with a number of transcription factors and transcriptional coactivators, e.g. p300/CBP, p53, YY1, and NF-κB, and coactivate transcription by methylating arginine 3 of histone H4.

Although PRMT1 is involved in cellular signaling, its aberrant activity has been implicated in heart disease and cancer. As the major PRMT in vivo, PRMT1 produces the majority of cellular ADMA. Upon proteolysis, free ADMA is released and competes with L-arginine for binding to nitric oxide synthases, thereby inhibiting these enzymes. This results in a decrease in the amount of NO, an important cell signaling molecule that increases vasodilation as illustrated in FIG. 3. Patients suffering from atherosclerosis, hypercholesterolemia and congestive heart failure have elevated levels of ADMA in the plasma and also show an increased expression of PRMT1. This seemingly causal relationship is further bolstered by studies with mice that are incapable of synthesizing dimethylarginine diaminohydrolase 1 (DDAH1). These knock-out mice exhibit increased serum levels of ADMA, reduced NO signaling, elevated systemic and pulmonary blood pressure and endothelial dysfunction. Apparently, if the elevated levels of ADMA could be decreased, then the synthesis of NO would be increased, leading to improved vascular homeostasis.

Likewise, excessive PRMT1 activity has recently been implicated in breast cancer. Hypermethylated ERα has been observed in some breast tumors, suggesting that the dysregulation of ERα methylation, may be involved in breast cancer development [15]. PRMT1 is known to interact with and regulate the transcriptional activity of the estrogen receptor [16]. Le Romancer et al. have demonstrated that hormone binding to the estrogen receptor stimulates PRMT1 to methylate ERα, primarily at arginine 260 in vitro and in vivo [15]. Concurrently, FAK (focal adhesion kinase-1) is partially dephosphorylated, inducing its interaction with the tyrosine kinase, Src, and subsequently the formation of a macromolecular complex, composed of ERα, Src, FAK and p85. This complex formation activates the protein kinase Akt (also known as protein kinase B), which is involved in cellular survival pathways. The indirect upregulation of Akt by PRMT1 activity is thought to be involved in the survival and proliferation of breast cancer cells. Thus, inhibitors that potently and selectively inhibit PRMT1 could potentially be used to regulate PRMT1 methylation activity, and serve as therapeutics for heart disease and breast cancer.

As such, a need exists for an irreversible inhibitor, targeting protein arginine methyltransferase 1.

SUMMARY

In accordance with certain embodiments of the present disclosure, a protein arginine methyltransferase inhibitor is provided. The inhibitor comprises an amino acid peptide joined to a chloroacetamidine warhead.

In still other embodiments of the present disclosure, a protein arginine methyltransferase inhibitor is provided comprising:

(SEQ ID NO: 1)

Ser-Gly-Orn-Gly-Lys-Gly-Gly-Lys-Gly-Leu-Gly-Lys-Gly-Gly-Ala-Lys-Arg-His-Arg-Lys-Val-COOH.

In still other embodiments of the present disclosure, a protein arginine methyltransferase inhibitor is provided comprising:

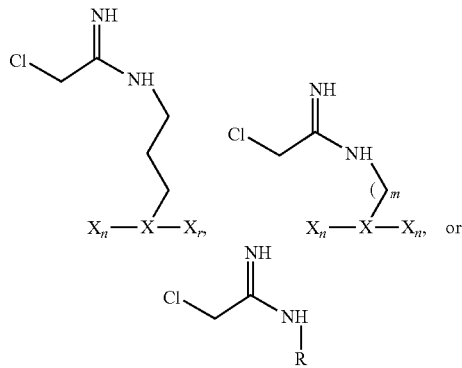

wherein each X comprises a separate amino acid, n comprises the number of amino acids, m comprises the number of methylene units, and R comprises a substituent.

In yet another embodiment of the present disclosure, a method of identifying a protein arginine methyltransferase inhibitor is provided. The method includes incubating protein arginine methyltransferase with one or more activity-based protein profiling reagents, at least one reagent comprising an amino acid peptide joined to a chloroacetamidine warhead, the reagent further comprising a fluorescent molecule.

In yet another embodiment of the present disclosure, a method of inhibiting protein arginine methyltransferase is provided. The method includes exposing protein arginine methyltransferase to an inhibitor comprising an amino acid peptide joined to a chloroacetamidine warhead.

Other features and aspects of the present disclosure are discussed in greater detail below.

BRIEF DESCRIPTION OF THE DRAWINGS

A full and enabling disclosure, including the best mode thereof, directed to one of ordinary skill in the art, is set forth more particularly in the remainder of the specification, which makes reference to the appended figures in which:

FIG. 4 discloses SEQ ID NO: 1;

DETAILED DESCRIPTION

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

Figure 1:
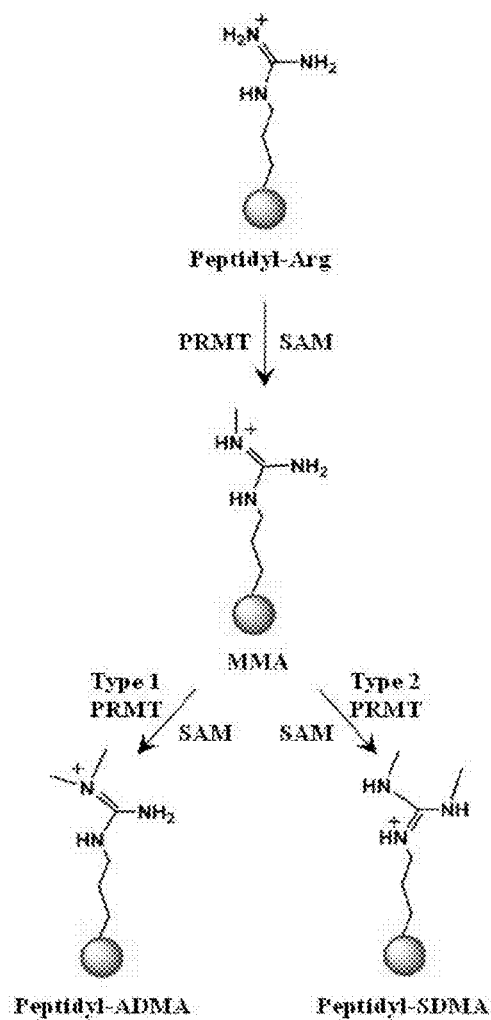
FIG. 1 illustrates PRMT-catalyzed mono- and di-methylation of peptidyl-arginine to form monomethyl arginine (MMA) and either asymmetric dimethyl arginine (ADMA) or symmetric dimethyl arginine (SDMA)
Figure 2:
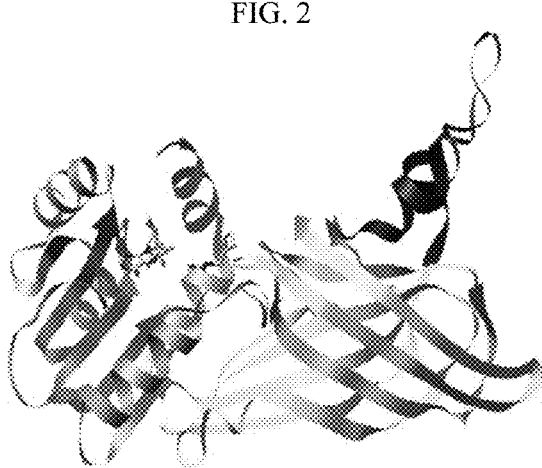
FIG. 2 illustrates the ribbon structure of PRMT1; the SAM-binding domain is in the bottom left portion of the illustration, β-barrel domain is in the bottom right portion of the illustration and the dimerization arm is in the upper right portion of the illustration with the structures of SAH and arginine are shown in sticks mode; the figure was generated with UCSF Chimera using the coordinates for the rat PRMT1•SAH•RGG3 peptide complex (PDB ID 1OR8)
Figure 3:
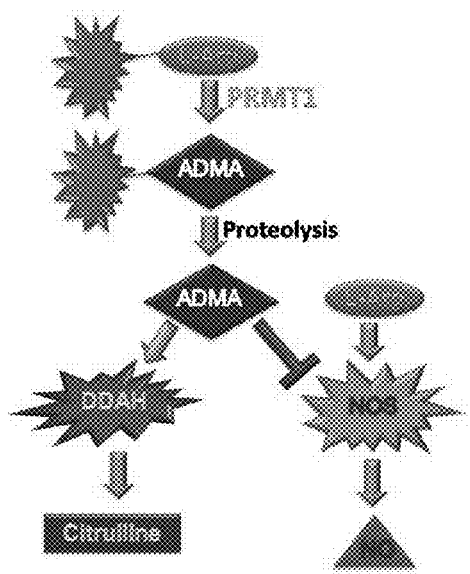
FIG. 3 illustrates the proposed role of PRMT1 in heart disease.
Figure 4:
FIG. 4 illustrates an inhibitor structure in accordance with certain embodiments of the present disclosure.

The present disclosure is generally directed to a potent, irreversible inhibitor, targeting protein arginine methyltransferase 1. The inhibitor comprises a 21 amino acid peptide and a chloro-acetamidine warhead in place of the guanidinium on the substrate arginine residue. One embodiment of an inhibitor structure in accordance with the present disclosure is illustrated in FIG. 4. Inhibition studies have demonstrated that the inhibitor is a potent and selective inactivator of the enzyme. The inhibitor has been found to covalently modify an active site residue on the enzyme. This compound can ultimately be optimized to generate therapeutic agents for the treatment of heart disease and breast cancer.

As discussed previously, the indirect upregulation of Akt by PRMT1 activity is thought to be involved in the survival and proliferation of breast cancer cells. Because PRMT1 activity is dysregulated in heart disease and cancer, the inhibitors described herein can be useful for the treatment of heart disease and cancer. The inhibitors and activity based probes described herein will also be useful for studying the in vivo role of PRMT1 activity.

In addition to PRMT1, there is significant evidence that the methyltransferase activity of other PRMTs is dysregulated in cancer. This evidence includes the fact that PRMT4/CARM1 is overexpressed in breast and prostate cancer. Overexpression of PRMT4/CARM1 likely increases cellular proliferation because it acts as a transcriptional coactivator for the Androgen and Estrogen Receptors. Because its methyltransferase activity is required for coactivation, PRMT4/CARM1 inhibitors will likely possess therapeutic value for a broad range of hormone-dependent cancers. Consistent with this idea is the fact that siRNA knockdown of PRMT4/CARM1 inhibits proliferation and induces apoptosis in prostate cancer cells.

PRMTs 5 and 7 also represent potential targets for the development of anticancer chemotherapeutics because overexpression of PRMT5 promotes anchorage independent cell growth. Additionally, decreased expression of PRMT7 correlates with resistance to cisplatinum and the topoisomerase II inhibitors 9-OH-E, S6020-2, and etoposide, and increased sensitivity to the cytotoxic effects of UV radiation, bleomycin, and camptothecin. In total, these results suggest that PRMT7 inhibitors could be used in combination with UV radiation, bleomycin, and camptothecin as an adjuvant therapy.

Figure 12:
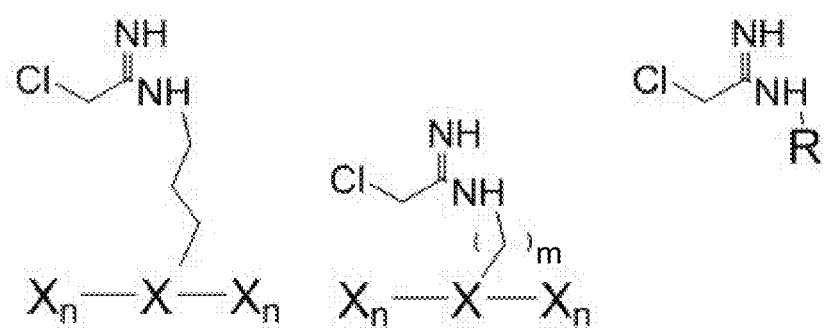
FIG. 12 illustrates potential inhibitor structures in accordance with certain embodiments of the present disclosure.

The inhibitors of the present disclosure are contemplated for inhibition of other PRMTs that can be optimized to generate therapeutic agents for the treatment of a variety of conditions. In this regard, because other PRMTs show significant homology to PRMT1, it must be appreciated that chloroacetamidine containing analogues of the compounds described herein will inhibit these enzymes. FIG. 12 is illustrative of certain example compounds. Referring to FIG. 12, X can comprise any amino acid, n refers to any number of amino acids, m comprises the number of methylene units, and R refers to any substituent, for instance an aryl or alkyl chain.

The potential derivatives depicted in FIG. 12 can also be useful for inhibiting PRMT1 and therefore be useful for the treatment of heart disease and cancer.

Because other PRMTs are also involved in human diseases, e.g. cancer, chloroacetamidine containing compounds will likely inhibit other PRMTs and be useful for the treatment of cancer.

In addition, fluorescently labeled activity based probes can be used in a fluorescence polarization assay that can be useful for a highthroughput screen that can be used to identify PRMT inhibitors from large libraries of compounds.

The present disclosure can be better understood with reference to the following examples.

EXAMPLES

Initially, the substrate specificity of PRMT1 was studied and a minimal peptide substrate was identified. These studies were performed using peptide substrates, based on a major substrate of the enzyme, i.e. histone H4. PRMT1 methylates the third arginine residue of the peptide substrate with a similar affinity to the relatively unstructured N-terminus of the full-length protein. The minimal substrate comprises of the first 21 amino acids of histone H4, and has an acetylated N-terminus as illustrated in FIG. 4. Considering the high affinity of the peptide toward the enzyme, the attachment of a chloroacetamidine warhead to the peptide was thought to convert the substrate into an inactivator.

Figure 5:
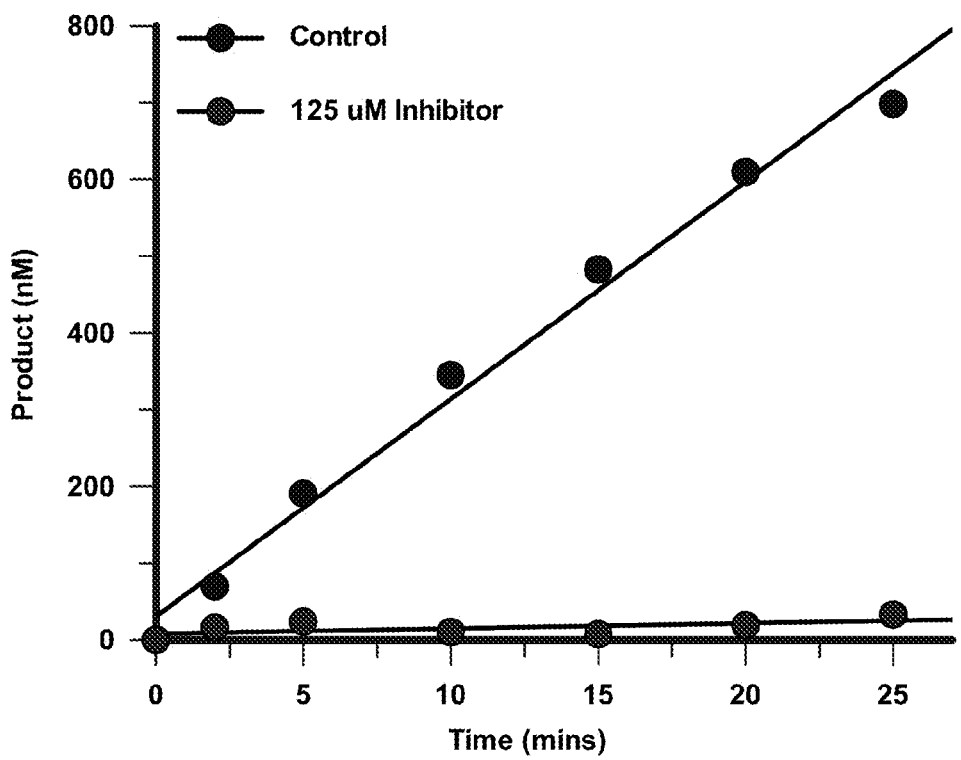
FIG. 5 illustrates a time course of enzyme:inhibitor complex following 20 hour dialysis.
Figure 6:
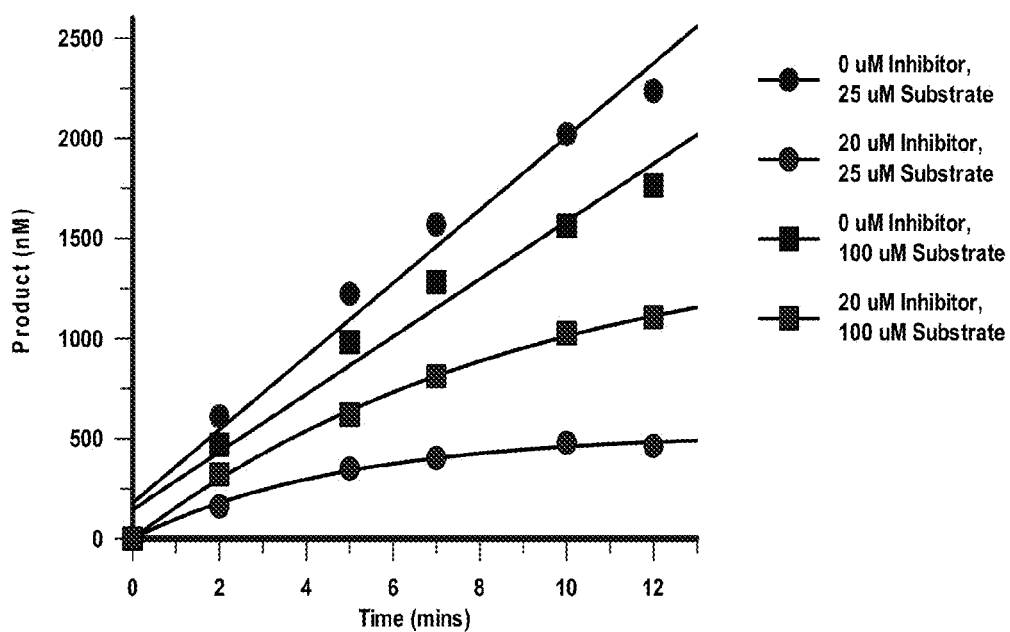
FIG. 6 illustrates substrate protection with ACH4-21 as substrate.

Subsequent rapid dilution assays and dialysis experiments confirmed that the inhibitor was covalently attaching to and inactivating the enzyme as illustrated in FIG. 5. FIG. 5 shows the preformed enzyme:inhibitor complex remains intact following overnight dialysis. The substrate protection assays, seen in FIG. 6, are consistent with the modification of an active site residue. This is the case because as the concentration of substrate is increased, the inhibition of the enzyme can be decreased. Note that enzymatic assays were performed as previously described in Osborne, T. C., et al., Protein arginine methyltransferase 1: positively charged residues in substrate peptides distal to the site of methylation are important for substrate binding and catalysis, Biochemistry, 2007, 46(46): p. 13370-81 and Obianyo, O., T. C. Osborne, and P. R. Thompson, Kinetic mechanism of protein arginine methyltransferase 1, Biochemistry, 2008, 47(39): p. 10420-7, both incorporated by reference herein.

Figure 7:
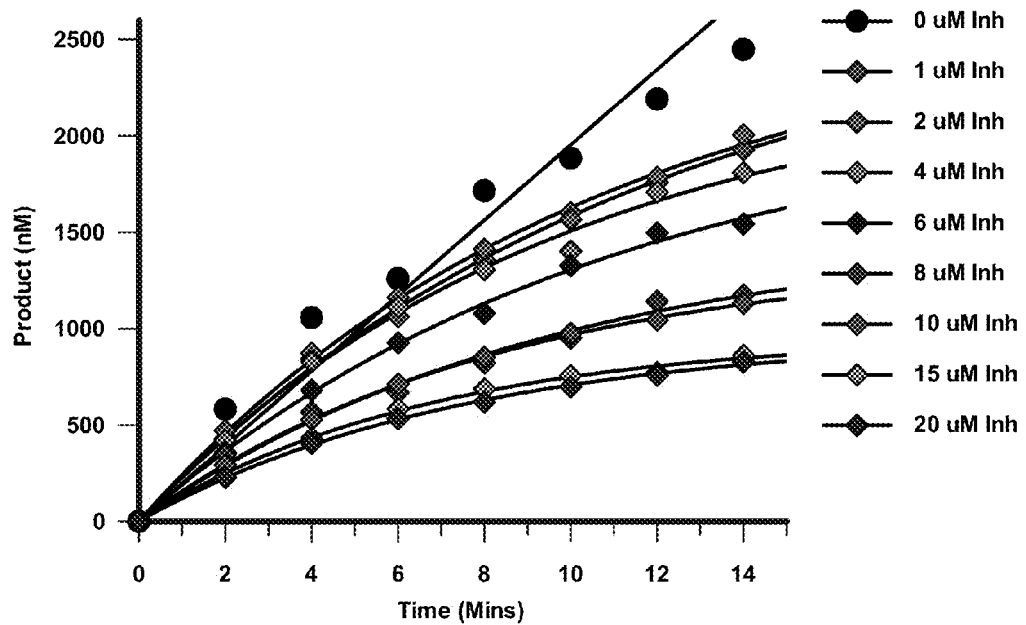
FIG. 7 illustrates product formation as a function of time over various inhibitor concentrations.
Figure 8:
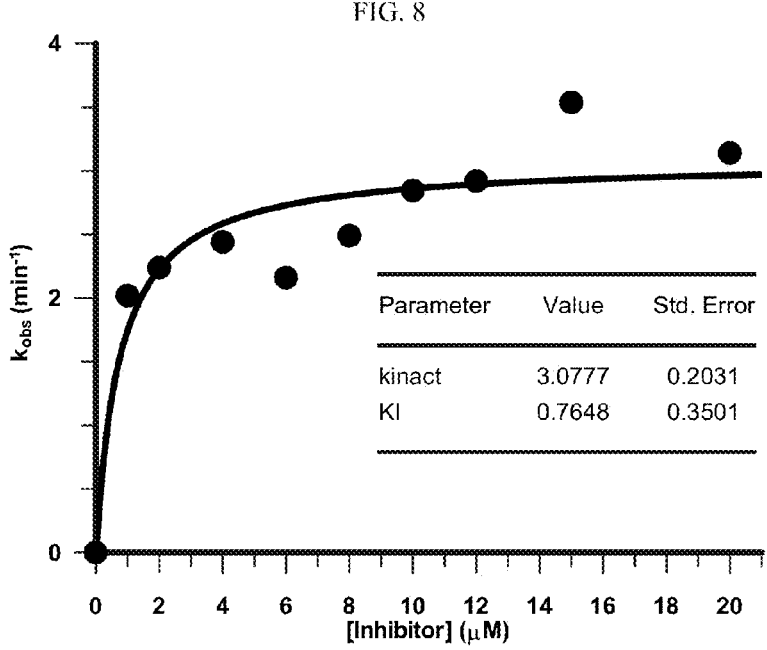
FIG. 8 illustrates Determination of $k_{inact}/K_I$ by plotting $k_{obs}$ against inhibitor concentrations.

Next, the potency of the inhibitor was examined Due to its ability to irreversibly inactivate PRMT1, the $k_{inact}/K_I$ value was determined as this value is the best indicator of an inactivator's potency, as shown in FIGS. 7 and 8. For these experiments, product formation as a function of time was measured over different inhibitor concentrations. The resulting nonlinear progress curves were fit to the following equation, $[Product]=v_i(1-e^{-k_{obst}})/k_{obs}$, to determine the pseudo-first order rate constant of inactivation. These values were corrected to generate true $k_{obs}$ values using the equation, $k_{obs}=(1+S)/K_M*k_{obs(apparent)}$. Plots of these values versus inhibitor concentration were then fit to the equation, $k_{obs}=k_{inact}[I]/(K_I+[I])$, to yield a curved line and the $k_{inact}/K_I$ value of $4.02\times10^6$ $min^{-1}\cdot M^{-1}$ as seen in FIG. 8.

Figure 9:
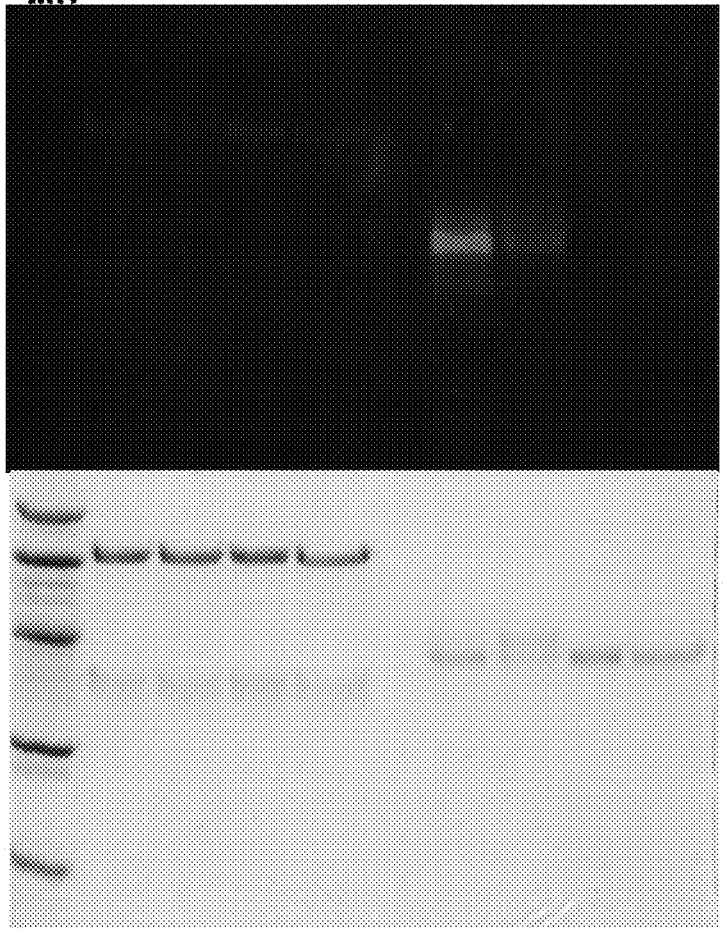
FIG. 9 illustrates labeling PRMT1 and PAD4 with fluorescent inhibitors; Cl-21 is the untagged inhibitor and Fitc-Cl-21 is the inhibitor with the fluorescent tag; 2 μM PRMT1 or PAD4 was reacted with 2 μM of either fluorescent compound for 30 minutes and unlabeled inhibitor, at 10 μM, was added to compete with the fluorescent inhibitor when indicated.
Figure 10:
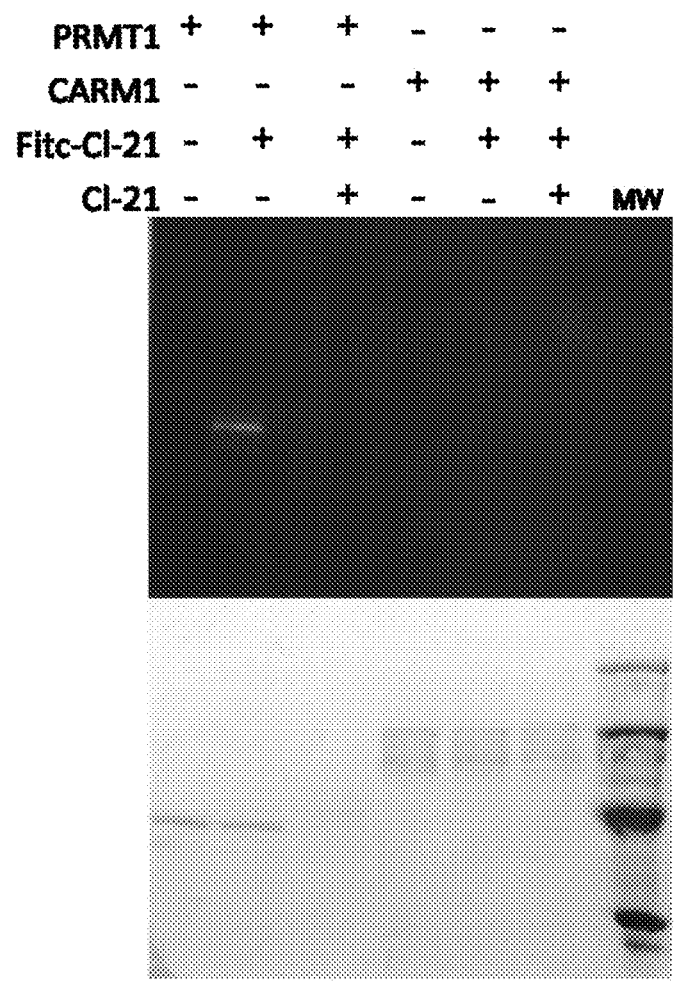
FIG. 10 illustrates selective labeling of PRMT1; 1 μM PRMT1 or CARM1 was reacted with 1 μM Fitc-Cl-21 for 30 minutes and the fluorescent probe competed with 100 μM of the untagged inhibitor for binding when stated.
Figure 11:
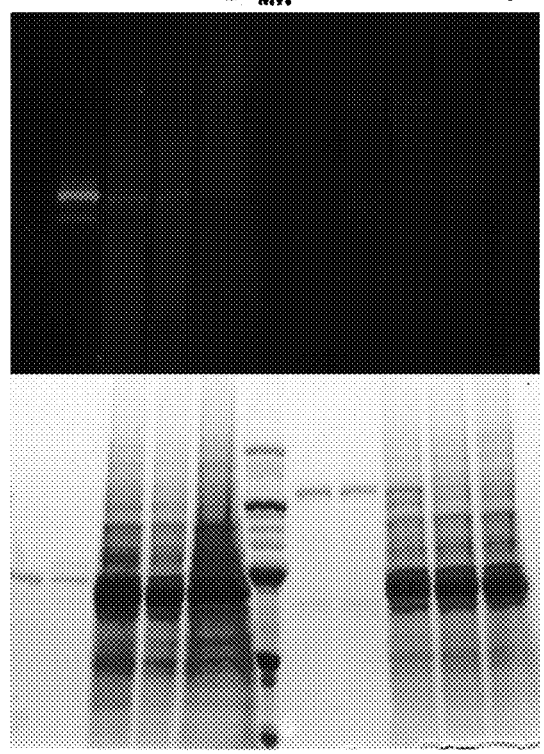
FIG. 11 illustrates labeling PRMT1 in MCF-7 whole cell extracts; 2 μg of purified PRMT1, PAD4, and/or 100 μg of whole cell extracts were reacted with 2 μM Fitc-Cl-21 for 30 minutes; the fluorescent probe competed with 1 mM of untagged inhibitor for binding, when indicated.

Additionally, the inhibitor has been modified by the addition of a fluorescent molecule, fluoresceinisothiocyanate (fitc), to enable the compound to be used as an activity-based protein profiling reagent. However, any suitable fluorophore or molecule that can signal labeling can be utilized. For instance, in certain embodiments, biotin can be utilized. The fluorescent compound has been used to label PRMT1, both in vitro and in vivo. In FIG. 9, PRMT1 or PAD4 was incubated with either the fluorescently tagged inhibitor (Fitc-Cl-21), or the fluorescent derivative of a potent PAD4 inhibitor, Cl-amidine (Fite-Cl-Am). The Fitc-Cl-21 was observed to bind strongly to PRMT1 and only weakly to PAD4. The binding of the fluorescent molecule also seemed to be attenuated by the untagged inhibitor, suggesting that the binding can be outcompeted. The fluorescent probe was also found to label PRMT1 but not PRMT4/CARM1 as seen in FIG. 10. FIG. 11 demonstrates that the fluorescent compound is able to label a protein around the same molecular weight as PRMT1 in whole cell extracts of MCF-7, human breast cancer cells. These studies demonstrate the utility of the inhibitor as a probe of PRMT1 activity.

In the interests of brevity and conciseness, any ranges of values set forth in this specification are to be construed as written description support for claims reciting any sub-ranges having endpoints which are whole number values within the specified range in question. By way of a hypothetical illustrative example, a disclosure in this specification of a range of 1-5 shall be considered to support claims to any of the following sub-ranges: 1-4; 1-3; 1-2; 2-5; 2-4; 2-3; 3-5; 3-4; and 4-5.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only, and is not intended to limit the disclosure.

We claim:

1. A method of identifying a protein arginine methyltransferase inhibitor comprising incubating protein arginine methyltransferase with one or more activity-based protein profiling reagents, at least one reagent comprising peptide joined to a chloroacetamidine warhead, wherein the peptide comprises the first 21 amino acids of histone H4, the reagent further comprising a fluorescent molecule.

2. The method of claim 1, wherein the fluorescent molecule comprises fluorophore, namely, fluoresceinoisothiocyanate, or biotin, or combinations thereof.

3. The method of claim 1, wherein more than one reagent comprises peptide joined to a chloroacetamidine warhead and a fluorescent molecule.

4. A method of inhibiting protein arginine methyltransferase comprising exposing protein arginine methyltransferase to an inhibitor comprising an amino acid peptide joined to a chloroacetamidine warhead, wherein the peptide comprises the first 21 amino acids of histone H4.

* * * * *